United States Patent
Okusawa

(10) Patent No.: US 11,368,647 B2
(45) Date of Patent: Jun. 21, 2022

(54) MEDICAL IMAGE RECORDING CONTROL APPARATUS, MEDICAL IMAGE RECORDING CONTROL SYSTEM, AND MEDICAL IMAGE RECORDING CONTROL METHOD

(71) Applicant: OLYMPUS CORPORATION, Tokyo (JP)

(72) Inventor: Yasuhiro Okusawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/331,749

(22) Filed: May 27, 2021

(65) Prior Publication Data
US 2021/0314522 A1    Oct. 7, 2021

Related U.S. Application Data

(63) Continuation of application No. PCT/JP2018/043722, filed on Nov. 28, 2018.

(51) Int. Cl.
*H04N 5/77*     (2006.01)
*A61B 1/00*     (2006.01)
(Continued)

(52) U.S. Cl.
CPC ........... *H04N 5/77* (2013.01); *A61B 1/00006* (2013.01); *G16H 40/20* (2018.01); *G16H 40/60* (2018.01)

(58) Field of Classification Search
None
See application file for complete search history.

(56) References Cited

U.S. PATENT DOCUMENTS

2006/0183972 A1*   8/2006   Tashiro ............... A61B 1/0004
                                                    600/101
2008/0122924 A1    5/2008   Tashiro
(Continued)

FOREIGN PATENT DOCUMENTS

EP    1870827 A1    12/2007
EP    3095378 A1    11/2016
(Continued)

OTHER PUBLICATIONS

International Search Report dated Jan. 29, 2019 issued in PCT/JP2018/043722.

*Primary Examiner* — Hung Q Dang
(74) *Attorney, Agent, or Firm* — Scully, Scott, Murphy & Presser, P.C.

(57) ABSTRACT

A medical image recording control apparatus includes a processor, a video source switching instruction circuit, and a video source switching device. The processor detects states of a plurality of devices and determines, from a detection result of the states of the plurality of devices, based on states of two or more devices including at least one of a room light, a surgical light, and a light source apparatus for endoscope included in the plurality of devices, a priority level of at least one video source device among a plurality of video source devices included in the plurality of devices. The video source switching instruction circuit generates a switching instruction signal corresponding to the determined priority level. The video source switching device receives the switching instruction signal, switches a video signal outputted to a video signal corresponding to the switching instruction signal, and outputs the video signal.

8 Claims, 11 Drawing Sheets

| No. | DEVICE STATE | | SCENE | ROOM CAMERA | SURGICAL CAMERA | CAMERA APPARATUS FOR LAPAROSCOPE |
|---|---|---|---|---|---|---|
| 1 | ROOM LIGHT | FULLY LIT | 1 | PRIORITY 1 | PRIORITY 2 | PRIORITY 3 |
|  | SURGICAL LIGHT | OFF | | | | |
|  | LIGHT SOURCE APPARATUS FOR LAPAROSCOPE | OFF | | | | |
|  | INSUFFLATION APPARATUS | AIR FEEDING STOPPED | | | | |
| 2 | ROOM LIGHT | OTHER THAN FULLY LIT | 2 | PRIORITY 2 | PRIORITY 1 | PRIORITY 3 |
|  | SURGICAL LIGHT | ON | | | | |
|  | LIGHT SOURCE APPARATUS FOR LAPAROSCOPE | OFF | | | | |
|  | INSUFFLATION APPARATUS | AIR FEEDING STOPPED | | | | |
| 3 | ROOM LIGHT | OTHER THAN FULLY LIT | 3 | PRIORITY 3 | PRIORITY 1 | PRIORITY 2 |
|  | SURGICAL LIGHT | ON | | | | |
|  | LIGHT SOURCE APPARATUS FOR LAPAROSCOPE | ON | | | | |
|  | INSUFFLATION APPARATUS | AIR FEEDING STOPPED | | | | |
| 4 | ROOM LIGHT | OTHER THAN FULLY LIT | 4 | PRIORITY 3 | PRIORITY 2 | PRIORITY 1 |
|  | SURGICAL LIGHT | ON | | | | |
|  | LIGHT SOURCE APPARATUS FOR LAPAROSCOPE | ON | | | | |
|  | INSUFFLATION APPARATUS | AIR FEEDING | | | | |

(51) Int. Cl.
  *G16H 40/20* (2018.01)
  *G16H 40/60* (2018.01)
  *A61B 1/06* (2006.01)
  *A61B 1/045* (2006.01)
  *H04N 9/80* (2006.01)
  *H04N 5/225* (2006.01)
  *H04N 7/18* (2006.01)

(56) References Cited

U.S. PATENT DOCUMENTS

| | | | |
|---|---|---|---|
| 2008/0163293 A1* | 7/2008 | Krummheller | H04N 21/472 |
| | | | 348/E7.071 |
| 2016/0338570 A1 | 11/2016 | Okusawa et al. | |
| 2018/0054476 A1* | 2/2018 | Kyser | A61B 5/0013 |
| 2020/0268471 A1* | 8/2020 | Kajita | H04N 5/23299 |

FOREIGN PATENT DOCUMENTS

| | | | |
|---|---|---|---|
| JP | 2004312468 A | * | 11/2004 |
| JP | 2005-135344 A | | 5/2005 |
| JP | 2007-336358 A | | 12/2007 |
| JP | 2008-282 A | | 1/2008 |
| JP | 2016-7444 A | | 1/2016 |
| JP | 2017-006260 A | | 1/2017 |
| WO | 2016/021232 A1 | | 2/2016 |

\* cited by examiner

FIG. 3

| No. | DEVICE STATE | | SCENE | ROOM CAMERA | SURGICAL CAMERA | CAMERA APPARATUS FOR LAPAROSCOPE |
|---|---|---|---|---|---|---|
| 1 | ROOM LIGHT | FULLY LIT | 1 | | PRIORITY 2 | PRIORITY 3 |
| | SURGICAL LIGHT | OFF | | PRIORITY 1 | | |
| | LIGHT SOURCE APPARATUS FOR LAPAROSCOPE | OFF | | | | |
| | INSUFFLATION APPARATUS | AIR FEEDING STOPPED | | | | |
| 2 | ROOM LIGHT | OTHER THAN FULLY LIT | 2 | PRIORITY 2 | PRIORITY 1 | PRIORITY 3 |
| | SURGICAL LIGHT | ON | | | | |
| | LIGHT SOURCE APPARATUS FOR LAPAROSCOPE | OFF | | | | |
| | INSUFFLATION APPARATUS | AIR FEEDING STOPPED | | | | |
| 3 | ROOM LIGHT | OTHER THAN FULLY LIT | 3 | PRIORITY 3 | PRIORITY 1 | PRIORITY 2 |
| | SURGICAL LIGHT | ON | | | | |
| | LIGHT SOURCE APPARATUS FOR LAPAROSCOPE | ON | | | | |
| | INSUFFLATION APPARATUS | AIR FEEDING STOPPED | | | | |
| 4 | ROOM LIGHT | OTHER THAN FULLY LIT | 4 | PRIORITY 3 | PRIORITY 2 | PRIORITY 1 |
| | SURGICAL LIGHT | ON | | | | |
| | LIGHT SOURCE APPARATUS FOR LAPAROSCOPE | ON | | | | |
| | INSUFFLATION APPARATUS | AIR FEEDING | | | | |

TBL

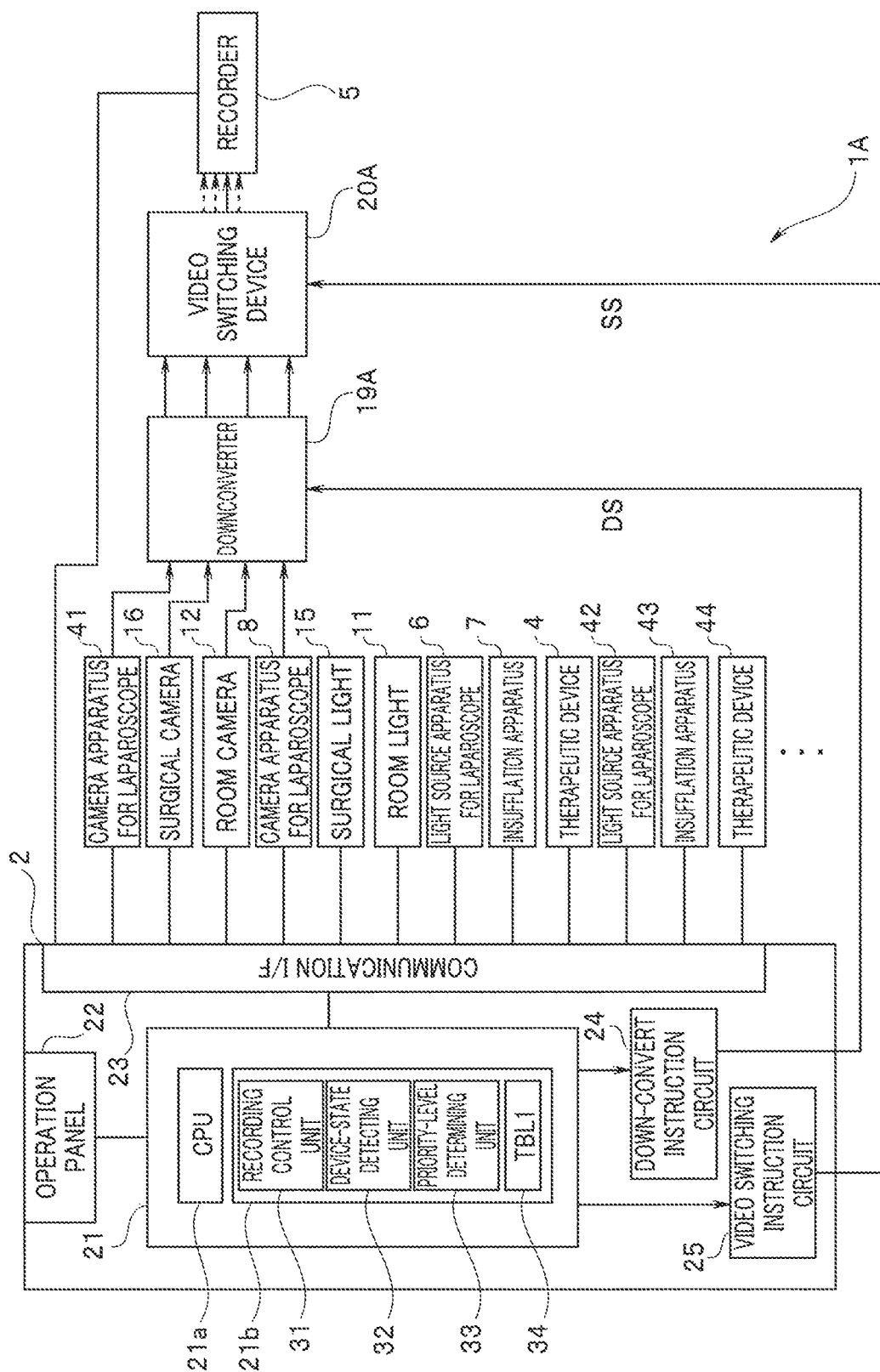

FIG. 7

TBL1

| No. | Device State | | Scene | Room Camera | Surgical Camera | First Camera Apparatus for Laparoscope | Second Camera Apparatus for Laparoscope |
|---|---|---|---|---|---|---|---|
| 1 | Room Light | Fully Lit | 1 | Priority 1 | Priority 2 | Priority 3 | Priority 4 |
| | Surgical Light | OFF | | | | | |
| | First Light Source Apparatus for Laparoscope | OFF | | | | | |
| | Second Light Source Apparatus for Laparoscope | OFF | | | | | |
| | First Insufflation Apparatus | Air Feeding Stopped | | | | | |
| | Second Insufflation Apparatus | Air Feeding Stopped | | | | | |
| | First Therapeutic Device | OFF | | | | | |
| | Second Therapeutic Device | OFF | | | | | |
| 2 | Room Light | Other than Fully Lit | 2 | Priority 2 | Priority 1 | Priority 3 | Priority 4 |
| | Surgical Light | ON | | | | | |
| | First Light Source Apparatus for Laparoscope | OFF | | | | | |
| | Second Light Source Apparatus for Laparoscope | OFF | | | | | |
| | First Insufflation Apparatus | Air Feeding Stopped | | | | | |
| | Second Insufflation Apparatus | Air Feeding Stopped | | | | | |
| | First Therapeutic Device | OFF | | | | | |
| | Second Therapeutic Device | OFF | | | | | |
| 3 | Room Light | Other than Fully Lit | 3 | Priority 3 | Priority 1 | Priority 2 | Priority 4 |
| | Surgical Light | ON | | | | | |
| | First Light Source Apparatus for Laparoscope | ON | | | | | |
| | Second Light Source Apparatus for Laparoscope | OFF | | | | | |
| | First Insufflation Apparatus | Air Feeding Stopped | | | | | |
| | Second Insufflation Apparatus | OFF | | | | | |
| | First Therapeutic Device | OFF | | | | | |
| | Second Therapeutic Device | OFF | | | | | |
| 4 | Room Light | Other than Fully Lit | 4 | Priority 3 | Priority 2 | Priority 1 | Priority 4 |
| | Surgical Light | ON | | | | | |
| | First Light Source Apparatus for Laparoscope | ON | | | | | |
| | Second Light Source Apparatus for Laparoscope | OFF | | | | | |
| | First Insufflation Apparatus | Air Feeding | | | | | |
| | Second Insufflation Apparatus | Air Feeding Stopped | | | | | |
| | First Therapeutic Device | ON | | | | | |
| | Second Therapeutic Device | OFF | | | | | |

FIG. 8

| No. | DEVICE STATE | | SCENE | ROOM CAMERA | SURGICAL CAMERA | FIRST CAMERA APPARATUS FOR LAPAROSCOPE | SECOND CAMERA APPARATUS FOR LAPAROSCOPE |
|---|---|---|---|---|---|---|---|
| 5 | ROOM LIGHT | OTHER THAN FULLY LIT | 5 | PRIORITY 4 | PRIORITY 2 | PRIORITY 1 | PRIORITY 3 |
|   | SURGICAL LIGHT | ON | | | | | |
|   | FIRST LIGHT SOURCE APPARATUS FOR LAPAROSCOPE | ON | | | | | |
|   | SECOND LIGHT SOURCE APPARATUS FOR LAPAROSCOPE | ON | | | | | |
|   | FIRST INSUFFLATION APPARATUS | AIR FEEDING | | | | | |
|   | SECOND INSUFFLATION APPARATUS | AIR FEEDING STOPPED | | | | | |
|   | FIRST THERAPEUTIC DEVICE | ON | | | | | |
|   | SECOND THERAPEUTIC DEVICE | OFF | | | | | |
| 6 | ROOM LIGHT | OTHER THAN FULLY LIT | 6 | PRIORITY 4 | PRIORITY 3 | PRIORITY 1 | PRIORITY 2 |
|   | SURGICAL LIGHT | ON | | | | | |
|   | FIRST LIGHT SOURCE APPARATUS FOR LAPAROSCOPE | ON | | | | | |
|   | SECOND LIGHT SOURCE APPARATUS FOR LAPAROSCOPE | ON | | | | | |
|   | FIRST INSUFFLATION APPARATUS | AIR FEEDING | | | | | |
|   | SECOND INSUFFLATION APPARATUS | ON | | | | | |
|   | FIRST THERAPEUTIC DEVICE | OFF | | | | | |
|   | SECOND THERAPEUTIC DEVICE | OFF | | | | | |
| 7 | ROOM LIGHT | OTHER THAN FULLY LIT | 7 | PRIORITY 4 | PRIORITY 3 | PRIORITY 2 | PRIORITY 1 |
|   | SURGICAL LIGHT | ON | | | | | |
|   | FIRST LIGHT SOURCE APPARATUS FOR LAPAROSCOPE | ON | | | | | |
|   | SECOND LIGHT SOURCE APPARATUS FOR LAPAROSCOPE | ON | | | | | |
|   | FIRST INSUFFLATION APPARATUS | AIR FEEDING | | | | | |
|   | SECOND INSUFFLATION APPARATUS | ON | | | | | |
|   | FIRST THERAPEUTIC DEVICE | OFF | | | | | |
|   | SECOND THERAPEUTIC DEVICE | ON | | | | | |
| 8 | ROOM LIGHT | OTHER THAN FULLY LIT | 8 | PRIORITY 4 | PRIORITY 2 | PRIORITY 3 | PRIORITY 1 |
|   | SURGICAL LIGHT | ON | | | | | |
|   | FIRST LIGHT SOURCE APPARATUS FOR LAPAROSCOPE | ON | | | | | |
|   | SECOND LIGHT SOURCE APPARATUS FOR LAPAROSCOPE | ON | | | | | |
|   | FIRST INSUFFLATION APPARATUS | AIR FEEDING | | | | | |
|   | SECOND INSUFFLATION APPARATUS | AIR FEEDING STOPPED | | | | | |
|   | FIRST THERAPEUTIC DEVICE | OFF | | | | | |
|   | SECOND THERAPEUTIC DEVICE | ON | | | | | |

TBL1

FIG. 10

TBL2

| No. | DEVICE STATE | | | | SCENE | ROOM CAMERA | SURGICAL CAMERA | CAMERA APPARATUS FOR LAPAROSCOPE | CAMERA APPARATUS FOR ENDOSCOPE |
|---|---|---|---|---|---|---|---|---|---|
| | ROOM LIGHT | SURGICAL LIGHT | LIGHT SOURCE APPARATUS FOR LAPAROSCOPE / LIGHT SOURCE APPARATUS FOR ENDOSCOPE | INSUFFLATION APPARATUS / FIRST THERAPEUTIC DEVICE / SECOND THERAPEUTIC DEVICE | | | | | |
| 1 | FULLY LIT | OFF | OFF / OFF | AIR FEEDING STOPPED / OFF / OFF | 1 | PRIORITY 1 | PRIORITY 2 | PRIORITY 3 | PRIORITY 4 |
| 2 | OTHER THAN FULLY LIT | ON | OFF / OFF | AIR FEEDING STOPPED / OFF / OFF | 2 | PRIORITY 2 | PRIORITY 1 | PRIORITY 3 | PRIORITY 4 |
| 3 | OTHER THAN FULLY LIT | ON | ON / OFF | AIR FEEDING STOPPED / OFF / OFF | 3 | PRIORITY 3 | PRIORITY 2 | PRIORITY 1 | PRIORITY 4 |
| 4 | OTHER THAN FULLY LIT | ON | ON / OFF | AIR FEEDING / ON / OFF | 4 | PRIORITY 3 | PRIORITY 2 | PRIORITY 1 | PRIORITY 4 |

FIG. 11

| No. | DEVICE STATE | | | | SCENE | ROOM CAMERA | SURGICAL CAMERA | CAMERA APPARATUS FOR LAPAROSCOPE | CAMERA APPARATUS FOR ENDOSCOPE |
|---|---|---|---|---|---|---|---|---|---|
| | ROOM LIGHT | OTHER THAN FULLY LIT | INSUFFLATION APPARATUS | AIR FEEDING | | | | | |
| 5 | SURGICAL LIGHT | ON | FIRST THERAPEUTIC DEVICE | ON | 5 | PRIORITY 3 | PRIORITY 4 | PRIORITY 1 | PRIORITY 2 |
| | LIGHT SOURCE APPARATUS FOR LAPAROSCOPE | ON | SECOND THERAPEUTIC DEVICE | OFF | | | | | |
| | LIGHT SOURCE APPARATUS FOR ENDOSCOPE | ON | | | | | | | |
| | ROOM LIGHT | OTHER THAN FULLY LIT | INSUFFLATION APPARATUS | AIR FEEDING | | | | | |
| 6 | SURGICAL LIGHT | ON | FIRST THERAPEUTIC DEVICE | ON | 6 | PRIORITY 3 | PRIORITY 4 | PRIORITY 2 | PRIORITY 1 |
| | LIGHT SOURCE APPARATUS FOR LAPAROSCOPE | ON | SECOND THERAPEUTIC DEVICE | ON | | | | | |
| | LIGHT SOURCE APPARATUS FOR ENDOSCOPE | ON | | | | | | | |
| | ROOM LIGHT | OTHER THAN FULLY LIT | INSUFFLATION APPARATUS | AIR FEEDING | | | | | |
| 7 | SURGICAL LIGHT | ON | FIRST THERAPEUTIC DEVICE | ON | 7 | PRIORITY 3 | PRIORITY 2 | PRIORITY 1 | PRIORITY 4 |
| | LIGHT SOURCE APPARATUS FOR LAPAROSCOPE | ON | SECOND THERAPEUTIC DEVICE | OFF | | | | | |
| | LIGHT SOURCE APPARATUS FOR ENDOSCOPE | OFF | | | | | | | |

TBL2

MEDICAL IMAGE RECORDING CONTROL APPARATUS, MEDICAL IMAGE RECORDING CONTROL SYSTEM, AND MEDICAL IMAGE RECORDING CONTROL METHOD

CROSS REFERENCE TO RELATED APPLICATION

This application is a continuation application of PCT/JP2018/043722 filed on Nov. 28, 2018, the entire contents of which are incorporated herein by this reference.

BACKGROUND OF THE INVENTION

1. Field of the Invention

The present invention relates to a medical image recording control apparatus, a medical image recording control system, and a medical image recording control method for recording a medical image.

2. Description of the Related Art

In a surgical operation, data and images of a patient are recorded. The recorded data and images are used to confirm, after the surgical operation, a procedure, a progress, and the like of the performed surgical operation. For example, Japanese Patent Application Laid-Open Publication No. 2005-135344 proposes a technique for recording videos of various cameras together with recording of various sensor data during a surgical operation.

Since various video sources such as a room camera, a surgical camera, and a laparoscope are present in an operation room, a video source to be recorded in a recording apparatus is switched according to a progress of a surgical operation to make it easy to confirm videos after the surgical operation.

SUMMARY OF THE INVENTION

A medical image recording control apparatus according to an aspect of the present invention includes a processor including hardware, a video source switching instruction circuit, and a video source switching device. The processor detects states of a plurality of devices including a medical device and determines, from a detection result of the states of the plurality of devices, based on states of two or more devices including at least one of a room light, a surgical light, and a light source apparatus for endoscope included in the plurality of devices, a priority level of at least one video source among a plurality of video sources included in the plurality of devices. The video source switching instruction circuit generates a switching instruction signal corresponding to the determined priority level of the at least one video source. The video source switching device receives the switching instruction signal, switches a video signal outputted out of the plurality of video sources to a video signal corresponding to the switching instruction signal, and outputs the video signal.

A medical image recording control system according to an aspect of the present invention includes a processor including hardware, a video source switching instruction circuit, a video source switching device, and a recording apparatus. The processor detects states of a plurality of devices including a medical device and determines, from a detection result of the states of the plurality of devices, based on states of two or more devices including at least one of a room light, a surgical light, and a light source apparatus for endoscope included in the plurality of devices, a priority level of at least one video source among a plurality of video sources included in the plurality of devices. The video source switching instruction circuit generates a switching instruction signal corresponding to the determined priority level of the at least one video source. The video source switching device receives the switching instruction signal, switches a video signal outputted out of the plurality of video sources to a video signal corresponding to the switching instruction signal, and outputs the video signal. The recording apparatus records at least one video signal outputted from the video source switching device.

A medical image recording control method according to an aspect of the present invention includes: detecting states of a plurality of devices including a medical device; determining, from a detection result of the states of the plurality of devices, based on states of two or more devices including at least one of a room light, a surgical light, and a light source apparatus for endoscope included in the plurality of devices, a priority level of at least one video source among a plurality of video sources included in the plurality of devices; generating a switching instruction signal corresponding to the determined priority level of the at least one video source; and receiving the switching instruction signal, switching a video signal outputted out of the plurality of video sources to a video signal corresponding to the switching instruction signal, and outputting the video signal.

BRIEF DESCRIPTION OF THE DRAWINGS

FIG. 3 is a diagram showing an example of a data structure of a table including priority information according to the embodiment of the present invention;

FIG. 6 is a block diagram showing a configuration relating to video recording in a medical system according to a modification 1 of the embodiment of the present invention;

FIG. 7 is a diagram showing an example of a data structure of a table including priority information according to the modification 1 of the embodiment of the present invention;

FIG. 8 is a diagram showing the example of the data structure of the table including the priority information according to the modification 1 of the embodiment of the present invention;

FIG. 10 is a diagram showing an example of a data structure of a table including priority information according to the modification 2 of the embodiment of the present invention; and FIG. 11 is a diagram showing the example of the data structure of the table including the priority information according to the modification 2 of the embodiment of the present invention.

DETAILED DESCRIPTION OF THE PREFERRED EMBODIMENT

The present invention is explained below with reference to an embodiment.

Figure 1:
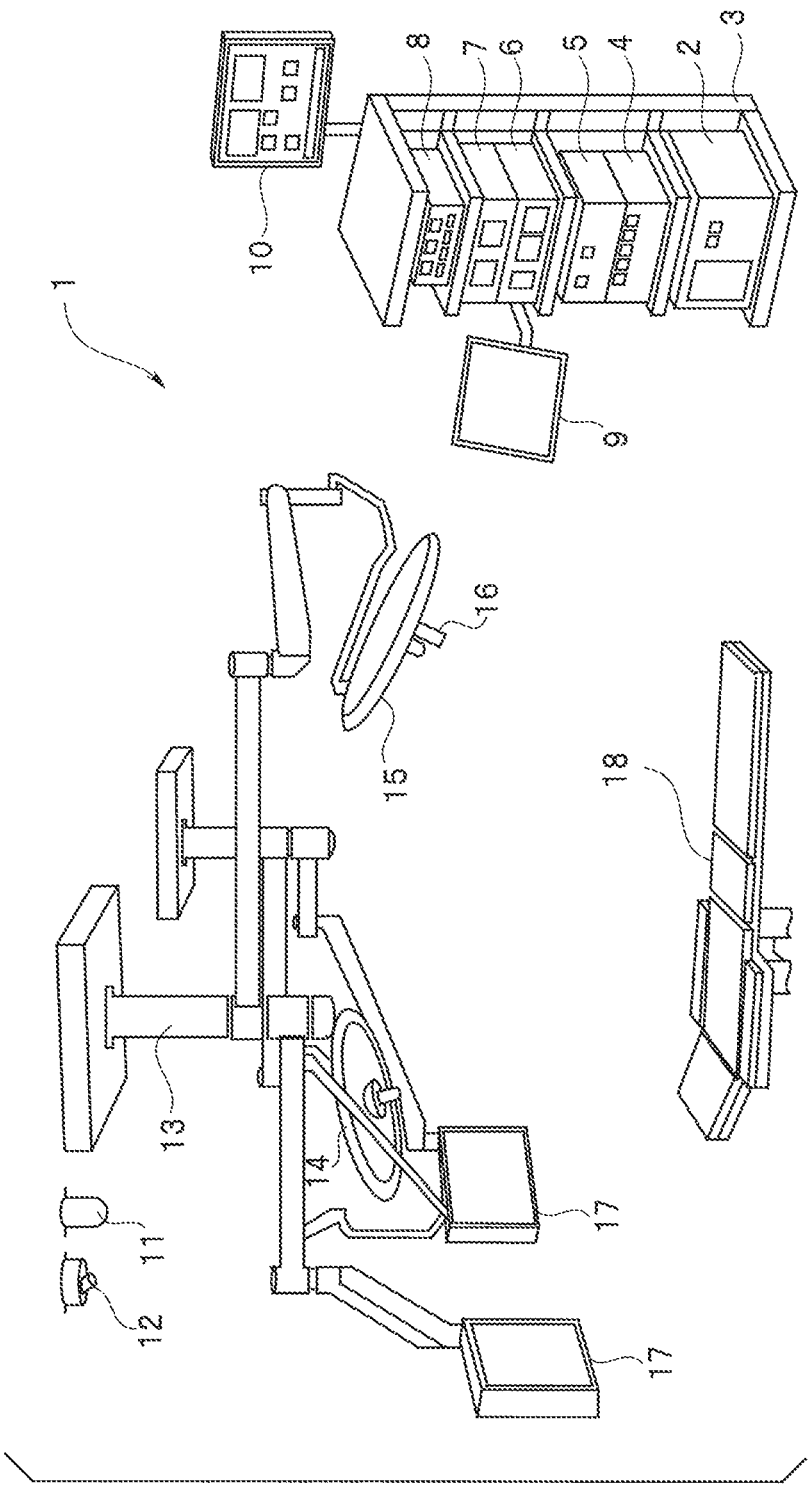
FIG. 1 is a diagram showing a setting state in an operation room of various devices included in a medical system according to an embodiment of the present invention.

FIG. 1 is a diagram showing a setting state in an operation room of various devices included in a medical system according to the embodiment. As shown in FIG. 1, a medical system 1 in the present embodiment includes a plurality of medical devices such as a camera apparatus for laparoscope and a therapeutic device and nonmedical devices such as a room camera and a room light. The medical system 1 may be provided in a room other than the operation room such as a consultation room.

The various devices of the medical system 1 are set in the operation room. The medical system 1 includes a system controller 2 that controls the various devices of the medical system 1. The system controller 2 is mounted on a rack 3 disposed in the operation room.

Besides the system controller 2, a therapeutic device such as an electric knife, a recorder 5 capable of recording videos, a light source apparatus for laparoscope 6, an insufflation apparatus 7 for inflating a body cavity of a patient, a camera apparatus for laparoscope 8 to which a laparoscope (not shown) inserted into the body cavity of the patient is connected, an operation panel apparatus 9 for operating the respective devices in the medical system 1, and a display panel 10 that displays various kinds of information such as output data of a desired device are also mounted on the rack 3.

A not-shown carbon dioxide cylinder is connected to the insufflation apparatus 7. Carbon dioxide gas is supplied into an abdomen of the patient via an insufflation tube extending from the insufflation apparatus 7 to a not-shown patient.

The laparoscope is a type of an endoscope. The camera apparatus for laparoscope 8 outputs, to a downconverter 19 explained below, a video signal of an image obtained by the laparoscope inserted into the body cavity of the patient.

On a ceiling of the operation room, a room light 11 for illuminating the operation room and a room camera 12 for picking up an image of the entire operation room are set.

An arm apparatus 13 is fixed on the ceiling of the operation room. Surgical lights 14 and 15, a surgical camera 16, and two monitors 17 are fixed to respective arms of the arm apparatus 13.

The surgical light 15 illuminates a surgical site of a patient on a bed 18. The surgical camera 16 picks up an image of the surgical site of the patient illuminated by the surgical light 15. An endoscopic video picked up by the laparoscope and a surgical site video picked up by the surgical camera 16 are displayed on the two monitors 17. The endoscopic video is a video of an observation part in a subject made incident through an observation window provided at a distal end portion of an insertion section of the not-shown laparoscope.

In the operation room, in addition to the devices explained above, a downconverter 19 and a video switching device 20 (FIG. 2) explained below are also set and can be controlled by the system controller 2.

A surgeon, a nurse, or the like operates the operation panel apparatus 9 to thereby cause necessary various devices to be operated according to a scene of a surgical operation and performs a surgical operation, that is, a medical action.

During the surgical operation, a selected video among a video obtained by the room camera 12, a video obtained by the surgical camera 16, and a video obtained by the camera apparatus for laparoscope 8 is recorded in the recorder 5, which is a video recording apparatus.

Figure 2:
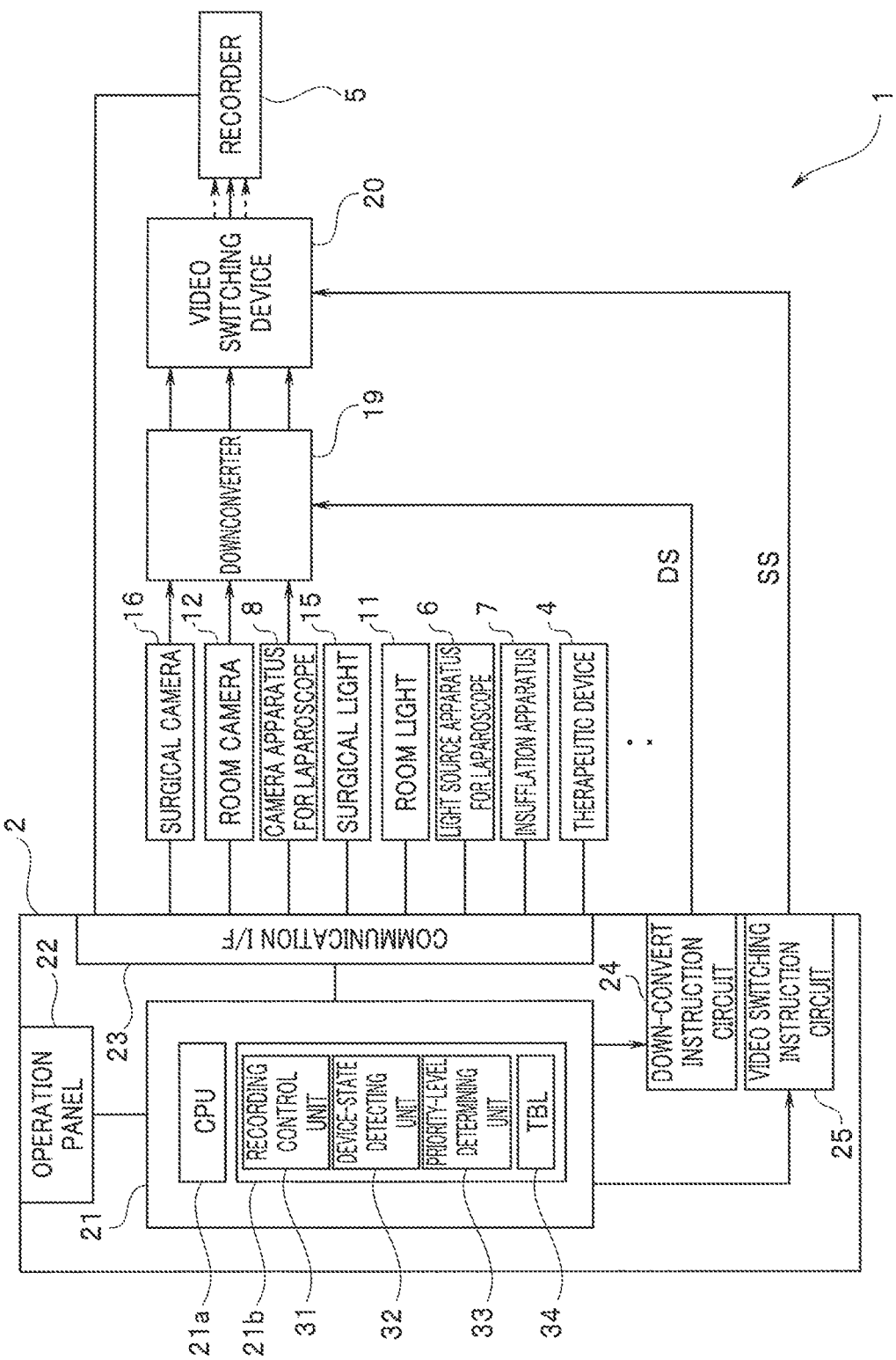
FIG. 2 is a block diagram showing a configuration relating to video recording in the medical system according to the embodiment of the present invention.

FIG. 2 is a block diagram showing a configuration relating to video recording in the medical system 1. The system controller 2 is connected to the downconverter 19 and the video switching device 20 as well in addition to the various devices explained above such as the surgical camera 16.

The downconverter 19 is connected to three video sources, that is, the surgical camera 16, the room camera 12, and the camera apparatus for laparoscope 8. The downconverter 19 down-converts at least one video signal among three video signals from the three video sources according to a downconverter instruction signal DS from the system controller 2.

The down-converting is processing for converting the number of pixels and a frequency into a lower-order signal standard from an original video signal.

Accordingly, the downconverter 19 is an apparatus capable of down-converting video signals of all or a part of a plurality of video sources to be converted into video signals having a lower-order number of pixels or a lower frequency.

A storage capacity of the down-converted video signal is smaller than a storage capacity of the original video signal not down-converted. The downconverter 19 outputs three video signals including at least one down-converted video signal to the video switching device 20.

The video switching device 20 configures a video-source switching unit that selectively switches and outputs a plurality of video signals of a plurality of video source devices.

The video switching device 20 receives the three video signals from the downconverter 19 and outputs one input signal designated by a video switching instruction signal SS from the system controller 2 to the recorder 5. The video switching device 20 is a so-called switcher. In FIG. 2, each of the surgical camera 16, the room camera 12, and the camera apparatus for laparoscope 8 is a video source device.

The recorder 5 is a recording apparatus that records the at least one video signal outputted from the video switching device 20. In the present embodiment, since the number of input channels of the recorder 5 is one, the recorder 5 records one video signal outputted from the video switching device 20.

The system controller 2 includes a processor 21, an operation panel 22, a communication interface (hereinafter abbreviated as communication I/F) 23, a down-convert instruction circuit 24, and a video switching instruction circuit 25.

The processor 21 includes a central processing unit (hereinafter referred to as CPU) 21a, a storage apparatus 21b such as a ROM and a flash memory, and a not-shown RAM.

In the storage apparatus 21b, various software programs for controlling the various devices included in the medical system 1 are recorded. In FIG. 2, only a recording control unit 31, a device-state detecting unit 32, and a priority-level determining unit 33 are shown as programs stored in the storage apparatus 21b.

Further, the storage apparatus 21b includes a table-information storing unit 34 that stores information of a table TBL storing priority information explained below.

The recording control unit 31 performs processing for recording videos of designated one or more video sources in the recorder 5 using state information of the respective devices detected by the device-state detecting unit 32 and priority level information determined by the priority-level determining unit 33. The priority level is set for each video source device as priority explained below. As the priority is higher, a video source is capable of performing recording at higher resolution.

More specifically, the recording control unit 31 controls, based on a priority level of at least one video source device determined in the priority-level determining unit 33 explained below, the video switching device 20 to output a video signal of the at least one video source device. Further, the recording control unit 31 controls, based on the determined at least one priority level, the downconverter 19 to down-convert video signals of the video source devices having priority levels other than a highest priority level.

The device-state detecting unit 32 performs processing for performing communication with the respective devices via the communication I/F 23 and detecting states of the respective devices. A state of a device is, for example, whether a power supply of the device is ON or OFF, an operation state or an output state of the device, or the like. For example, the state of the device is brightness of the room light 11 and an output state of the therapeutic device 4. In other words, the device-state detecting unit 32 detects states of a plurality of devices including a medical device.

The priority-level determining unit 33 refers to the table TBL of the table-information storing unit 34 and performs, based on the states of the respective devices detected by the device-state detecting unit 32, processing for determining priority levels of the respective video sources. In particular, the priority-level determining unit 33 determines, from a detection result of the device-state detecting unit 32, based on states of two or more devices including at least one of the room light 11, the surgical light 15, and the light source apparatus for laparoscope 6 included in the plurality of devices, a priority level of at least one video source device among the plurality of video source devices included in the plurality of devices.

The operation panel 22 is a user interface apparatus including an operation button for a user to perform various kinds of setting. For example, the operation panel 22 is a display including a touch panel apparatus. A surgeon or the like, who is a user, can operate the operation panel 22 to set and change priority information of the table TBL.

The communication I/F 23 is a circuit that performs communication with the respective devices such as the surgical camera 16. The processor 21 outputs control signals to the respective devices and receives state signals and the like from the respective devices via the communication I/F 23.

The down-convert instruction circuit 24 outputs a down-convert instruction signal DS to the downconverter 19 according to a control signal from the processor 21.

As explained above, the downconverter 19 is an apparatus that receives video signals from the camera apparatus for laparoscope 8, the room camera 12, and the surgical camera 16 and converts, according to the down-convert instruction signal DS, a video of a designated video source into a video having designated low resolution.

The camera apparatus for laparoscope 8 and the surgical camera 16 can photograph a video of an object at 4K resolution. The room camera 12 can photograph a video of an object at full high-vision resolution. The 4K-resolution video is a video having screen resolution of approximately 4000×2000. The room camera 12 can photograph a video of an object at 2K resolution. Accordingly, the downconverter 19 can convert the 4K-resolution video into a 2K or 1K-resolution video and convert the 2K-resolution video into a 1K-resolution video.

4K-resolution video data has more data amount than 2K-resolution video data. A lot of storage capacity is necessary when the 4K-resolution video data is recorded in the recorder 5. Accordingly, the video data down-converted to 2K resolution has less data amount than the 4K-resolution video data. The video data further down-converted to 1K resolution has lesser data amount than the 2K-resolution video data.

For example, when the downconverter 19 has down-convert functions of a plurality of forms, the user sets a form of down-convert in the downconverter 19 in advance.

Accordingly, a storage capacity at the time when down-converted video data is stored in the recorder 5 is smaller than a storage capacity of the original video data.

The video switching instruction circuit 25 outputs a video switching instruction signal SS to the video switching device 20 according to a control signal from the processor 21. The video switching instruction signal SS is a signal for designating, that is, selecting a video signal to be outputted to the recorder 5 among three inputted video signals.

Note that, as the recorder, there are a recorder having only one input channel, a recorder having a plurality of input channels, a recorder having a function of separately recording two or more videos, a recorder having a function of combining two or more videos as one image, that is, one video, a recorder that records videos of all video sources, and the like.

Accordingly, the user sets, according to a type of the recorder 5, in the storage apparatus 21b, information RS about the number of output video sources about the number of video signals outputted by the video switching device 20. In other words, the user sets, in the storage apparatus 21b, the information RS indicating whether only one video is recorded, two videos are separately recorded, two videos are combined and recorded as one video, or videos of all video sources are recorded in the recorder 5.

For example, when the recorder 5 is a recorder capable of recording videos of a plurality of video sources, the user sets, in the recorder 5, videos of how many video sources are recorded. The set information RS is set in advance in the storage apparatus 21b.

Since the recorder 5 is the recorder having only one input channel, the information RS includes information indicating that the number of video sources to be recorded is one.

The video switching instruction circuit 25 selects, according to the video switching instruction signal SS, only a video signal of one of the three video sources, that is, the camera apparatus for laparoscope 8, the room camera 12, and the surgical camera 16 and outputs the video signal.

However, as explained above, the recorder 5 may have a plurality of input channels. If the recorder 5 has two input channels, the number of video source devices to be recorded is two or one. In that case, the recording control unit 31 refers to the set information RS and outputs a control signal to the video switching instruction circuit 25 based on the information RS. The video switching instruction circuit 25 outputs, according to the control signal, the video switching instruction signal SS for allocating a video signal of at least one video source device to an input channel corresponding to the video source device in descending order of a priority level of determined at least one video source device.

For example, as indicated by dotted lines, the recorder 5 sometimes has two or three input channels. When the recorder 5 has two input channels and the video switching device 20 has two output channels, based on the video switching instruction signal SS, the video switching device 20 outputs a video signal of a video source having priority 1 to an output channel 1 and outputs a video signal of a video source having priority 2 to an output channel 2.

If the recorder 5 has three input channels, the video switching device 20 has three output channels. Based on the video switching instruction signal SS, the video switching device 20 outputs a video signal of a video source having priority 1 to the output channel 1, outputs a video signal of a video source having priority 2 to the output channel 2, and outputs a video signal of a video source having priority 3 to an output channel 3.

Note that, even when the recorder 5 has two or more input channels, the video switching device 20 may not output video signals of video sources as many as the number of input channels of the recorder 5. The recorder 5 may not record video signals of all of the two or more input channels.

In other words, the video switching instruction circuit 25 configures a video-source-switching-instruction output unit that outputs, to the video switching device 20, the video switching instruction signal SS corresponding to a priority level of at least one video source device determined in the priority-level determining unit 33. As a result, only a video signal selected based on the video switching instruction signal SS in descending order of priority levels is inputted to and recorded in the recorder 5.

FIG. 3 is a diagram showing an example of a data structure of the table TBL including priority information.

In the table TBL shown in FIG. 3, priority information of three video sources in four scenes 1 to 4 is set. In other words, four kinds of setting information corresponding to the four scenes are set in the table TBL from the operation panel 22 by the user such as the surgeon.

In the scene 1, the room light 11 is in a fully lit state, the surgical light 15 and the light source apparatus for laparoscope 6 are in an OFF state, the insufflation apparatus 7 is in an air feeding stopped state. Accordingly, the scene 1 corresponds to a preparation state before a surgical operation or a state in which the surgical operation ends.

In the scene 1, priority of the room camera 12 is set to the highest "1", priority of the surgical camera 16 is set to "2", and priority of the camera apparatus for laparoscope 8 is set to "3".

In other words, the scene 1 corresponds to a situation before the surgical operation or after the surgical operation in which the surgical light 15 and the light source apparatus for laparoscope 6 are off. Accordingly, the priority of the room camera 12 that photographs the entire operation room is set to "1".

In the scene 2, the room light 11 is in a state other than the fully lit state, the surgical light 15 is in an ON state, the light source apparatus for laparoscope 6 is in the OFF state, and the insufflation apparatus 7 is in the air feeding stopped state. Accordingly, the scene 2 corresponds to a state immediately before the surgical operation is started or a state in which abdominal closure is performed.

In the scene 2, the priority of the surgical camera 16 is set to the highest "1", the priority of the room camera 12 is set to "2", and the priority of the camera apparatus for laparoscope 8 is set to "3".

In other words, the scene 2 corresponds to a situation in which the surgical light 15 is on, the light source apparatus for laparoscope 6 is off, and preparation for the surgical operation is made or the abdominal closure is performed. Accordingly, the priority of the surgical camera 16 that photographs the surgical site is set to "1".

In the scene 3, the room light 11 is in a state other than the fully lit state, the surgical light 15 and the light source apparatus for laparoscope 6 is in the ON state, and the insufflation apparatus 7 is in the air feeding stopped state. Accordingly, the scene 3 corresponds to a state in which preparation of the laparoscope is made.

In the scene 3, the priority of the surgical camera 16 is set to the highest "1", the priority of the camera apparatus for laparoscope 8 is set to "2", and the priority of the room camera 12 is set to "3".

In other words, the scene 3 corresponds to a situation in which preparation of the laparoscope is made because the light source apparatus for laparoscope 6 is in the ON state but the laparoscope is not used yet because the insufflation apparatus 7 is in set to "1".

In the scene 4, the room light 11 is in a state other than the fully lit state, the surgical light 15 and the light source apparatus for laparoscope 6 are in the ON state, and the insufflation apparatus 7 is in an air feeding state. Accordingly, the scene 4 corresponds to a situation in which the laparoscope is used.

In the scene 4, the priority of the camera apparatus for laparoscope 8 is set to the highest "1", the priority of the surgical camera 16 is set to "2", and the priority of the room camera 12 is set to "3".

In other words, in the scene 4, since the insufflation apparatus 7 is in the air feeding state and the laparoscope is used, the priority of the camera apparatus for laparoscope 8 is set to "1".

Note that, since the recorder 5 has only one input channel, as priority information indicating a priority level, only the priority "1" may be set in the table TBL.

As explained above, in the table TBL, the priority level of the at least one video source device is set according to the states of the two or more devices in the respective scenes in the surgical operation.

The table TBL is referred to based on the states of the devices when the priority-level determining unit 33 determines the priority levels of the respective video sources. Accordingly, the table-information storing unit 34 of the storage apparatus 21b that stores the table TBL configures a priority-level-information storing unit that stores priority level information of the at least one video source device set according to the states of the two or more devices.

When the surgical operation is performed by the medical system 1, the system controller 2 performs operation control for the various devices according to an instruction of the user such as the surgeon. The recording control unit 31 of the processor 21 uses the functions of the device-state detecting unit 32 and the priority-level determining unit 33 and performs necessary down-convert from video signals of the three video sources and records necessary one or more video signals in the recorder 5.

(Action)

The recording control unit 31, the device-state detecting unit 32, and the priority-level determining unit 33 are configured by the software programs as explained above. In the processor 21, the CPU 21a reads out the software programs from the storage apparatus 21b and executes the software programs to thereby function as the recording control unit 31, the device-state detecting unit 32, and the priority-level determining unit 33.

Note that all or a part of the functions of the recording control unit 31, the device-state detecting unit 32, and the priority-level determining unit 33 of the processor 21 may be configured as individual electronic circuits or may be configured as circuit blocks in an integrated circuit such as an FPGA (field programmable gate array).

In the present embodiment, for example, the processor 21 may include one or more CPUs.

Figure 4:
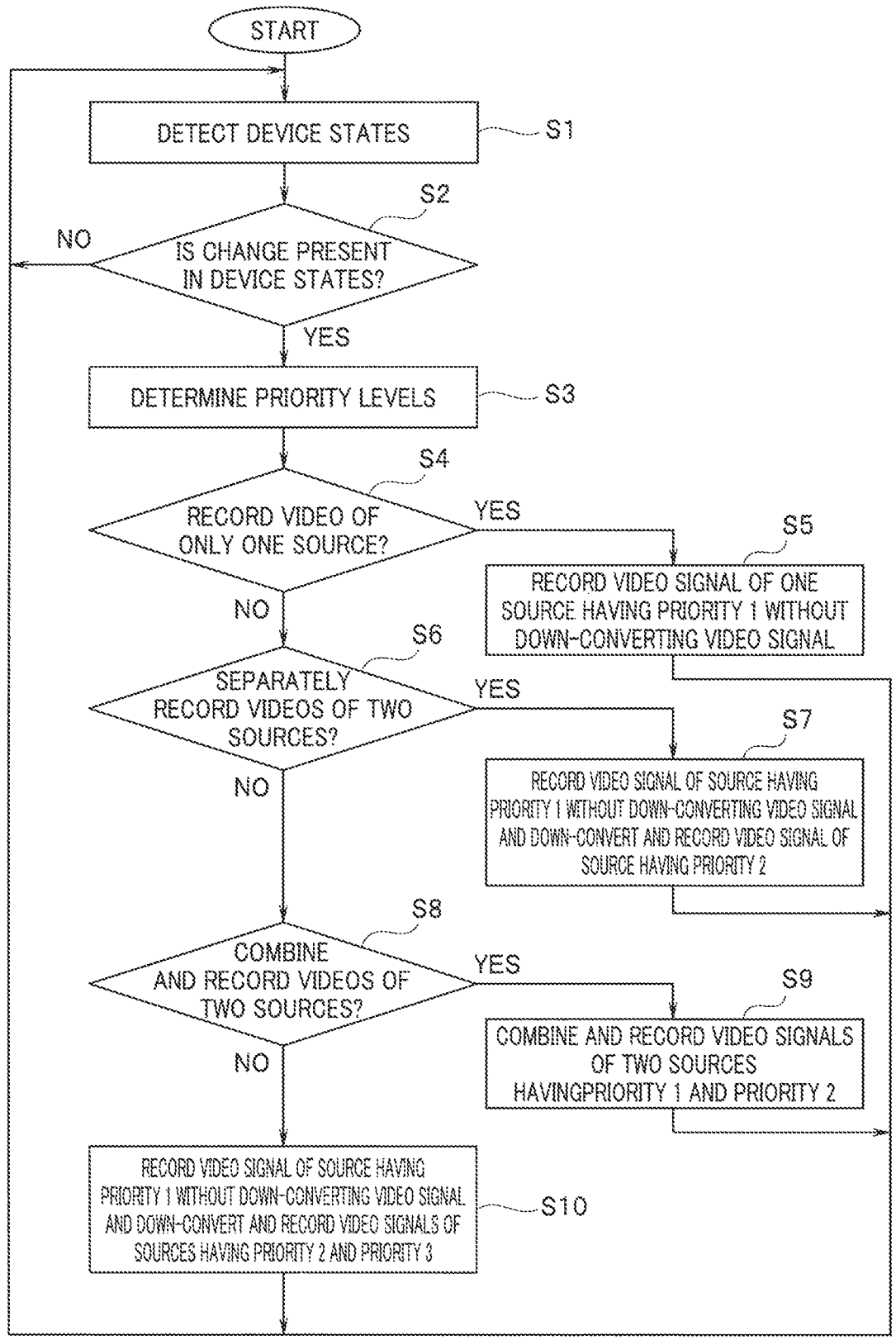
FIG. 4 is a flowchart showing an example of a flow of processing of a recording control unit according to the embodiment of the present invention.

FIG. 4 is a flowchart showing an example of a flow of processing of the recording control unit 31.

The processor 21 performs, with the device-state detecting unit 32, device state confirmation for confirming states of the respective devices of the medical system 1 (step (hereinafter abbreviated as S) 1). The device-state detecting unit 32 can perform communication with the respective devices via the communication I/F 23 and confirm the states of the respective devices. The states of the respective devices are ON and OFF of a power supply, an operation state, and the like.

After S1, the processor 21 determines whether there is a change in the states of the respective devices (S2). If there is no change in the states of the respective devices (S2: NO), the processing returns to S1.

When there is a change in the states of the respective devices (S2: YES), the processor 21 determines priority levels of the respective video sources with the priority-level determining unit 33 (S3).

The priority-level determining unit 33 refers to the table TBL and determines the priority levels of the respective video sources, that is, the room camera 12, the surgical camera 16, and the camera for laparoscope 8 based on states of the room light 11, the surgical light 15, the light source apparatus for laparoscope 6, and the insufflation apparatus 7.

For example, when a present situation is the scene 1 judging from the states of the respective devices, it is determined that the priority level of the room camera 12 is "1", the priority level of the surgical camera 16 is "2", and the priority level of the camera apparatus for laparoscope 8 is "3".

After S3, the processor 21 determines whether to record only a video of one video source in the recorder 5 (S4). The processor 21 performs the determination in S4 based on the recording form information explained above.

The information RS indicating that the recorder 5 has only one input channel is set in the storage apparatus 21b. Accordingly, the processor 21 determines YES in S4 and records a video signal of a video source having priority "1" without down-converting the video signal (S5).

In S5, the processor 21 transmits the down-convert instruction signal DS and the video switching instruction signal SS respectively to the downconverter 19 and the video switching device 20 to record only a video of one video source having a highest priority among the three video sources.

More specifically, the down-convert instruction signal DS is a signal for instructing to output the video signal of the video source having the priority "1" without down-converting the video signal and the video switching instruction signal SS is a signal for instructing to output the video signal of the video source having the priority "1". Accordingly, for example, in the scenes 2 and 3, the video signal of the surgical camera 16 is recorded at 4K resolution without being down-converted. In the scene 4, the video signal of the camera apparatus for laparoscope 8 is recorded at 4K resolution without being down-converted.

The down-convert instruction signal DS is a signal indicating that the video signal of the video source having the priority "1" is not down-converted. The video switching instruction signal SS is a signal for outputting the video signal of the video source having the priority "1" to the recorder 5.

After S5, the processing returns to S1.

If the recorder 5 has two input channels and the information RS is set to separately record videos of two video sources, the processor 21 determines NO in S4 and determines whether to separately record video signals of the two video sources (S6).

When the videos of the two video sources are separately recorded (S6: YES), the processor 21 transmits the down-convert instruction signal DS and the video switching instruction signal SS respectively to the downconverter 19 and the video switching device 20 to record a video signal of a video source having priority "1" in the recorder 5 without down-converting the video signal and down-convert a video signal of a video source having priority "2" and record the video signal in the recorder 5 (S7).

In S7, the down-convert instruction signal DS is a signal indicating that the video signal of the video source having the priority "1" is not down-converted and the video signal of the video source having the priority "2" is down-converted. The video switching instruction signal SS is a signal for outputting the video signals of the two video sources having the priority "1" and the priority "2" to the recorder 5.

For example, when the present situation is the scene 2 judging from the states of the respective devices, it is determined that the priority level of the surgical camera 16 is "1", the priority level of the room camera 12 is "2", and the priority level of the camera apparatus for laparoscope 8 is "3". Accordingly, a video signal of the surgical camera 16 is not down-converted and is inputted to the channel 1 of the recorder 5 and recorded at 4K resolution. A video signal of the room camera 12 is down-converted, inputted to the channel 2 of the recorder 5, and recorded at 1K resolution.

After S7, the processing returns to S1.

If the recorder 5 has two input channels and the information RS is set to combine videos of two video sources and record the videos, the processor 21 determines NO in S4 and S6 and determines whether to combine and record the videos of the two video sources (S8).

When the videos of the two video sources are combined and recorded (S8: YES), the processor 21 transmits the down-convert instruction signal DS and the video switching instruction signal SS respectively to the downconverter 19 and the video switching device 20 to combine and record the video signal of the video source having the priority "1" and the video signal of the video source having the priority "2" (S9).

The down-convert instruction signal DS is a signal indicating that the video signal of the video source having the priority "1" and the video signal of the video source having the priority "2" are not down-converted. The video switching instruction signal SS is a signal for outputting the video signals of the two video sources having the priority "1" and the priority "2" to the recorder 5.

In the recorder 5, the video signal of the video source having the priority "1" and the video signal of the video source having the priority "2" are combined. A combined video has resolution of a video having priority "1".

Figure 5:
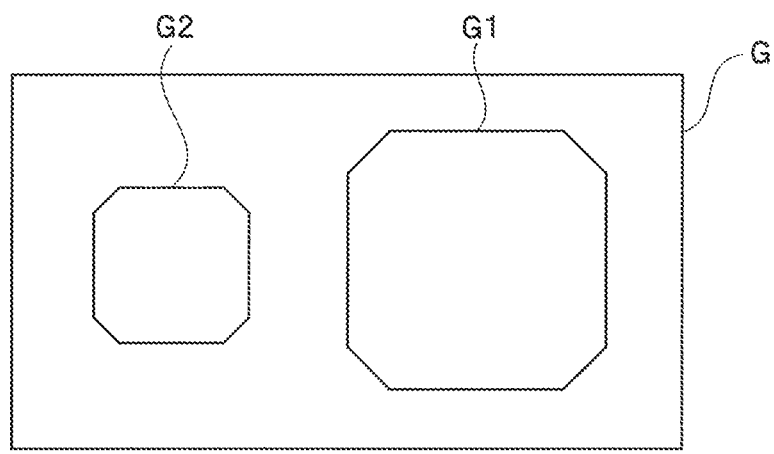
FIG. 5 is a diagram showing a display example of a combined video according to the embodiment of the present invention.

FIG. 5 is a diagram showing a display example of a combined video.

The recorder 5 combines two videos. A combined video is a video that can be displayed on a display screen of a display apparatus of a not-shown computer. As shown in FIG. 5, the combined video has, on a display screen G of the display apparatus, a video display region G1 corresponding to a video signal having priority "1" and a video display region corresponding to a video signal having priority "2". A size of the video display region G1 is larger than a size of the video display region G2.

The display apparatus is an apparatus capable of displaying a 4K-resolution video. For example, one combined video is generated in the recorder 5 such that the 4K-resolution video is displayed in the video display region G1 and a 2K-resolution video is displayed in the video display region G2. In other words, the display apparatus that displays combined two videos is in a so-called two-screen display state for displaying two videos at the same time point.

When the present situation is the scene 3 judging from the states of the respective devices, it is determined that the priority level of the surgical camera 16 is "1", the priority level of the camera apparatus for laparoscope 8 is "2", and the priority level of the room camera 12 is "3". Accordingly, the video signal of the surgical camera 16 is inputted to the channel 1 of the recorder 5 and the video signal of the camera apparatus for laparoscope 8 is inputted to the channel 2 of the recorder 5. The recorder 5 combines and records the two video signals such that, from the two video signals, a video of the surgical camera 16 is displayed in the video display region G1 and a video of the channel 2 of the room camera 12 is displayed in the video display region G2.

After S9, the processing returns to S1.

If the recorder 5 has three input channels and is set to record all videos of the three video sources (S8: YES), the processor 21 transmits the down-convert instruction signal DS and the video switching instruction signal SS respectively to the downconverter 19 and the video switching device 20 to output the video signal of the video source having the priority "1" to the recorder 5 without down-converting the video signal and down-convert the video signals of the video sources having the priority "2" and the priority "3" and output the video signals to the recorder 5 and separately record the video signals of the three video sources (S10).

The down-convert instruction signal DS is a signal indicating that the video signal of the video source having the priority "1" is not down-converted and the video signals of the video sources having the priority "2" and the priority "3" are down-converted. The video switching instruction signal SS is a signal for outputting the video signals of the three video sources having the priority "1", the priority "2", and the priority "3" to the recorder 5.

For example, when the present situation is the scene 4 judging from the states of the respective devices, it is determined that the priority level of the camera apparatus for laparoscope 8 is "1", the priority level of the surgical camera 16 is "2", and the priority level of the room camera 12 is "3". Accordingly, the video signal of the camera apparatus for laparoscope 8 is inputted to the channel 1 of the recorder 5 without being down-converted and recorded. The two video signals of the surgical camera 16 and the room camera 12 are down-converted and respectively inputted to the channels 2 and 3 of the recorder 5 and recorded.

After S10, the processing returns to S1.

As explained above, the priority levels are determined according to the states of the plurality of devices. The video sources to be recorded are selected according to the determined priority levels and the videos of the video sources are recorded.

Therefore, according to the embodiment explained above, since videos having high priority levels are recorded at high resolution, it is possible to realize a medical image recording control system that prevents a storage capacity necessary for the storage apparatus from increasing and automatically perform switching of a video source to be recorded.

In particular, a video having a low priority level is down-converted and stored with a small storage capacity and a video having a high priority level can be recorded at high resolution.

Subsequently, modifications of the embodiment explained above are explained.

In the embodiment explained above, the number of video sources is three, that is, the camera apparatus for laparoscope 8, the room camera 12, and the surgical camera 16. However, in the modifications explained below, a video source is added. The number of video sources is four.

(Modification 1)

FIG. 6 is a block diagram showing a configuration relating to video recording in a medical system 1A according to a modification 1.

In FIG. 6, the same components as the components shown in FIG. 2 are denoted by the same reference numerals and signs and explanation of the components is omitted.

The medical system 1A includes two laparoscopes and two therapeutic devices. More specifically, a first camera apparatus for laparoscope 8 and a second camera apparatus for laparoscope 41, a first light source apparatus for laparoscope 6 and a second light source apparatus for laparoscope 42, a first insufflation apparatus 7 and a second insufflation apparatus 43, and a first therapeutic device 4 and a second therapeutic device 44 are included in the medical system 1A.

Video sources are four video sources, that is, the first camera apparatus for laparoscope 8, the second camera apparatus for laparoscope 41, the room camera 12, and the surgical camera 16.

A downconverter 19A has the same function as the function of the downconverter 19 but has four input channels and four output channels.

FIG. 7 and FIG. 8 are diagrams showing an example of a data structure of a table TBL1 including priority information according to the modification 1.

In the table TBL1, priority information of the four video sources corresponding to eight states (eight scenes) of eight devices shown in FIG. 7 is set. The table TBL1 is stored in the table-information storing unit 34.

In a scene 1, the room light 11 is in the fully lit state but the other devices are not operated. The scene 1 corresponds to the scene 1 shown in FIG. 3 in the embodiment explained above.

Accordingly, in the scene 1, priority of the room camera 12 is set to the highest "1", priority of the surgical camera 16 is set to "2", priority of the first camera apparatus for laparoscope 8 is set to "3", and priority of the second camera apparatus for laparoscope 41 is set to "4".

In a scene 2, the room light 11 is in a state other than the fully lit state. The surgical light 15 is in an ON state and the other devices are not operated. The scene 2 corresponds to the scene 2 shown in FIG. 3 in the embodiment explained above.

Accordingly, in the scene 2, the priority of the surgical camera 16 is set to the highest "1", the priority of the room camera 12 is set to "2", the priority of the first camera apparatus for laparoscope 8 is set to "3", and the priority of the second camera apparatus for laparoscope 41 is set to "4".

In a scene 3, the room light 11 is in a state other than the fully lit state. The surgical light 15 and the first light source apparatus for laparoscope 6 are in the ON state and the other devices are not operated. The scene 3 corresponds to the scene 3 shown in FIG. 3 in the embodiment explained above.

Accordingly, in the scene 3, the priority of the surgical camera 16 is set to the highest "1", the priority of the first camera apparatus for laparoscope 8 is set to "2", the priority of the room camera 12 is set to "3", and the priority of the second camera apparatus for laparoscope 41 is set to "4".

In a scene 4, the room light 11 is in a state other than the fully lit state. The surgical light 15 and the first light source apparatus for laparoscope 6 are in the ON state, the first therapeutic device 4 is in the ON state, that is, an output state, the first insufflation apparatus 7 is in an air feeding state, and the other devices are not operated. The scene 4 corresponds to the scene 4 shown in FIG. 3 in the embodiment explained above.

Accordingly, in the scene 4, the priority of the first camera apparatus for laparoscope 8 is set to the highest "1", the priority of the surgical camera 16 is set to "2", the priority of the room camera 12 is set to "3", and the priority of the second camera apparatus for laparoscope 41 is set to "4".

In a scene 5, the second light source apparatus for laparoscope 42 is further in the ON state in the state of scene 4. The scene 5 corresponds to the scene 3 shown in FIG. 3 in the embodiment explained above.

Accordingly, in the scene 5, the priority of the first camera apparatus for laparoscope 8 is set to the highest "1", the priority of the surgical camera 16 is set to "2", the priority of the second camera apparatus for laparoscope 41 is set to "3", and the priority of the room camera 12 is set to "4".

In a scene 6, the second insufflation apparatus 43 is further in the air feeding state in the state of the scene 5. The scene 6 corresponds to the scene 4 shown in FIG. 3 in the embodiment explained above.

Accordingly, in the scene 6, the priority of the first camera apparatus for laparoscope 8 is set to the highest "1", the priority of the second camera apparatus for laparoscope 41 is set to "2", the priority of the surgical camera 16 is set to "3", and the priority of the room camera 12 is set to "4".

In a scene 7, the first therapeutic device 4 is turned off and the second therapeutic device 44 is in the output state in the state of the scene 6.

Accordingly, in the scene 7, the priority of the second camera apparatus for laparoscope 41 is set to the highest "1", the priority of the first camera apparatus for laparoscope 8 is set to "2", the priority of the surgical camera 16 is set to "3", and the priority of the room camera 12 is set to "4".

Note that when both of the first therapeutic device 4 and the second therapeutic device 44 change to the output state, already-set priority may not be changed or priority of the therapeutic device that changes to the output state later may be set to "1".

In a scene 8, the first insufflation apparatus 7 is in an air feeding stopped state in the state of the scene 7.

Accordingly, in the scene 8, the priority of the second camera apparatus for laparoscope 41 is set to the highest "1", the priority of the surgical camera 16 is set to "2", the priority of the first camera apparatus for laparoscope 8 is set to "3", and the priority of the room camera 12 is set to "4".

As explained above, according to this modification 1, the same effects as the effects in the embodiment can be obtained.

Note that, in this modification, since the two camera apparatuses for laparoscope 8 and 41 are used, in the case of the two-screen display shown in FIG. 5, the sizes of the two video display regions G1 and G2 are preferably set the same.

(Modification 2)

Figure 9:
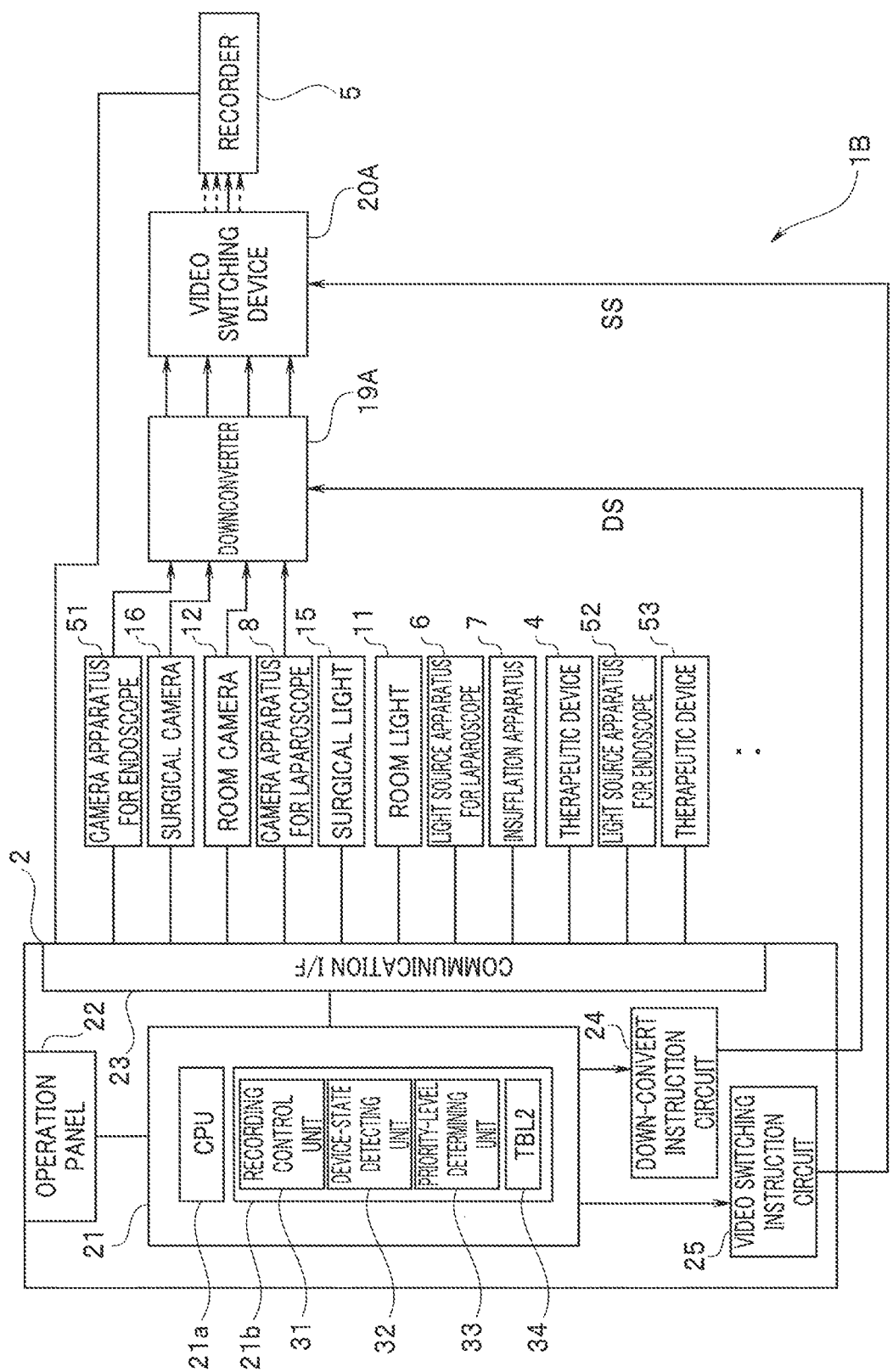
FIG. 9 is a block diagram showing a configuration relating to video recording in a medical system according to a modification 2 of the embodiment of the present invention.

FIG. 9 is a block diagram showing a configuration relating to video recording in a medical system 1B according to a modification 2.

In FIG. 9, the same components as the components shown in FIG. 2 and FIG. 5 are denoted by the same reference numerals and signs and explanation of the components is omitted.

The medical system 1B includes one laparoscope, one endoscope, and two therapeutic devices. More specifically, the camera apparatus for laparoscope 8 and a camera apparatus for endoscope 51, the light source apparatus for laparoscope 6 and a light source apparatus for endoscope 52, the insufflation apparatus 7, and the first therapeutic device 4 and a second therapeutic device 53 are included in the medical system 1B. The first therapeutic device 4 is used under observation by the camera apparatus for laparoscope 8. The second therapeutic device 53 is used under observation by the light source apparatus for endoscope 52.

Video sources are four video sources, that is, the camera apparatus for laparoscope 8, the camera apparatus for endoscope 51, the room camera 12, and the surgical camera 16.

A downconverter 19B has the same function as the function of the downconverter 19A in the modification 1 explained above.

FIG. 10 and FIG. 11 are diagrams showing an example of a data structure of a table TBL2 including priority information according to the modification 2.

In the table TBL2, priority information of the four video sources corresponding to seven states (seven scenes) of seven devices shown in FIG. 10 and FIG. 11 is set. The table TBL2 is stored in the table-information storing unit 34.

In a scene 1, the room light 11 is in the fully lit state but the other devices are not operated. The scene 1 corresponds to the scene 1 shown in FIG. 3 in the embodiment explained above.

Accordingly, in the scene 1, priority of the room camera 12 is set to the highest "1", priority of the surgical camera 16 is set to "2", priority of the camera apparatus for laparoscope 8 is set to "3", and priority of the camera apparatus for endoscope 51 is set to "4".

In a scene 2, the room light 11 is in a state other than the fully lit state. The surgical light 15 is in an ON state and the other devices are not operated. The scene 2 corresponds to the scene 2 shown in FIG. 3 in the embodiment explained above.

Accordingly, in the scene 2, the priority of the surgical camera 16 is set to the highest "1", the priority of the room camera 12 is set to "2", the priority of the camera apparatus for laparoscope 8 is set to "3", and the priority of the camera apparatus for endoscope 51 is set to "4".

In a scene 3, the room light 11 is in a state other than the fully lit state. The surgical light 15 and the light source apparatus for laparoscope 6 are in the ON state and the other devices are not operated. The scene 3 corresponds to the scene 3 shown in FIG. 3 in the embodiment explained above.

Accordingly, in the scene 3, the priority of the surgical camera 16 is set to the highest "1", the priority of the camera apparatus for laparoscope 8 is set to "2", the priority of the room camera 12 is set to "3", and the priority of the camera apparatus for endoscope 51 is set to "4".

In a scene 4, the room light 11 is in a state other than the fully lit state. The surgical light 15 and the light source apparatus for laparoscope 6 are in the ON state, the therapeutic device 4 is in the ON state, that is, an output state, the insufflation apparatus 7 is in an air feeding state, and the other devices are not operated. The scene 4 corresponds to the scene 4 shown in FIG. 3 in the embodiment explained above.

Accordingly, in the scene 4, the priority of the camera apparatus for laparoscope 8 is set to the highest "1", the priority of the surgical camera 16 is set to "2", the priority of the room camera 12 is set to "3", and the priority of the camera apparatus for endoscope 51 is set to "4".

In a scene 5, the camera apparatus for endoscope 51 is further in the ON state in the state of scene 4. The scene 5 corresponds to the scene 3 shown in FIG. 3 in the embodiment explained above.

Accordingly, in the scene 5, the priority of the camera apparatus for laparoscope 8 is set to the highest "1", the priority of the camera apparatus for endoscope 51 is set to "2", the priority of the room camera 12 is set to "3", and the priority of the surgical camera 16 is set to "4".

In a scene 6, the second therapeutic device 53 is further in the ON state, that is, the output state in the state of the scene 5. In the scene 6, since the therapeutic device 53 for endoscope is in the output state, the camera apparatus for endoscope 51 is more prioritized than the camera apparatus for laparoscope 8.

Accordingly, in the scene 6, the priority of the camera apparatus for endoscope 51 is set to the highest "1", the priority of the camera apparatus for laparoscope 8 is set to "2", the priority of the room camera 12 is set to "3", and the priority of the surgical camera 16 is set to "4".

In a scene 7, the light source apparatus for endoscope 52 and the second therapeutic device 53 are in an OFF state in the state of the scene 6. In the scene 7, since the use of the endoscope system is considered to end, the priority of the camera apparatus for endoscope 51 is set lowest.

Accordingly, in the scene 7, the priority of the camera apparatus for laparoscope 41 is set to the highest "1", the priority of the surgical camera 16 is set to "2", the priority of the room camera 12 is set to "3", and the priority of camera apparatus for endoscope 51 is set to "4".

As explained above, according to this modification 2, the same effects as the effects in the embodiment can be obtained.

Note that, in this modification 2, since the camera apparatus for laparoscope 8 and the camera apparatus for endoscope 51 are used, in the case of the two-screen display shown in FIG. 5, the sizes of the two video display regions G1 and G2 are preferably set the same.

Furthermore, in this modification 2, in the case of a procedure not using the therapeutic device 53, the priority of the camera apparatus for endoscope 51 is set lower than the priority of the camera apparatus for laparoscope 8.

As explained above, according to the embodiment and the respective modifications explained above, it is possible to provide a medical image recording control apparatus, a medical image recording control system, and a medical image recording control method for preventing a storage capacity necessary for a storage apparatus from increasing and automatically performing switching of a video source to be recorded.

The present invention is not limited to the embodiment explained above. Various changes, alternations, and the like are possible in a range in which the gist of the invention is not changed.

What is claimed is:

1. A medical image recording control apparatus comprising:
    a processor including hardware;
    a video source switching instruction circuit; and
    a video source switching device, wherein
    the processor detects states of a plurality of devices including a medical device and determines, from a detection result of the states of the plurality of devices, based on states of two or more devices including at least one of a room light, a surgical light, and a light source apparatus for endoscope included in the plurality of devices, a priority level of at least one video source among a plurality of video sources included in the plurality of devices,
    the video source switching instruction circuit generates a switching instruction signal corresponding to the determined priority level of the at least one video source, and
    the video source switching device receives the switching instruction signal, switches a video signal outputted out of the plurality of video sources to a video signal corresponding to the switching instruction signal, and outputs the video signal.

2. The medical image recording control apparatus according to claim 1, wherein the priority level of the at least one video source is set according to states of the two or more devices in respective scenes in a surgical operation.

3. The medical image recording control apparatus according to claim 1, further comprising a priority level information storage apparatus storing priority level information of the at least one video source set according to states of the two or more devices, wherein
    the processor refers to the priority level information storage apparatus and determines, based on the states of the two or more devices, a priority level of the at least one video source.

4. The medical image recording control apparatus according to claim 1, further comprising a downconverter capable of down-converting video signals of the plurality of video sources to be converted into video signals having a lower-order number of pixels or a lower frequency, wherein
    the processor controls, based on the determined priority level of the at least one video source, the video source switching device to output a video signal of the at least one video source and controls, based on the determined at least one priority level, the downconverter to down-convert a video signal of a video source having a priority level other than a highest priority level.

5. A medical image recording control system comprising:
    a processor including hardware;
    a video source switching instruction circuit;
    a video source switching device; and
    a recording apparatus, wherein
    the processor detects states of a plurality of devices including a medical device and determines, from a detection result of the states of the plurality of devices, based on states of two or more devices including at least one of a room light, a surgical light, and a light source apparatus for endoscope included in the plurality of devices, a priority level of at least one video source among a plurality of video sources included in the plurality of devices,
    the video source switching instruction circuit generates a switching instruction signal corresponding to the determined priority level of the at least one video source,
    the video source switching device receives the switching instruction signal, switches a video signal outputted out of the plurality of video sources to a video signal corresponding to the switching instruction signal, and outputs the video signal, and
    the recording apparatus records at least one video signal outputted from the video source switching device.

6. The medical image recording control system according to claim 5, wherein
    the recording apparatus includes a plurality of input channels, and the video source switching instruction circuit outputs the switching instruction signal for allocating a video signal of the at least one video source to the input channel corresponding to the video source device in descending order of the determined priority level of the at least one video source.

7. A medical image recording control method comprising:
detecting states of a plurality of devices including a medical device;
determining, from a detection result of the states of the plurality of devices, based on states of two or more devices including at least one of a room light, a surgical light, and a light source apparatus for endoscope included in the plurality of devices, a priority level of at least one video source among a plurality of video sources included in the plurality of devices;
generating a switching instruction signal corresponding to the determined priority level of the at least one video source; and
receiving the switching instruction signal, switching a video signal outputted out of the plurality of video sources to a video signal corresponding to the switching instruction signal, and outputting the video signal.

8. The medical image recording control method according to claim 7, further comprising receiving the switching instruction signal and recording at least one video signal outputted out of the plurality of video sources.

\* \* \* \* \*